United States Patent [19]

Ouellette et al.

[11] Patent Number: 5,728,058

[45] Date of Patent: Mar. 17, 1998

[54] ELASTIC KNEE WRAP

[75] Inventors: William R. Ouellette, Cincinnati; Timothy A. Burkett, West Chester; Leane K. Davis, Milford; Elizabeth M. Harvey, West Chester; Kurt E. Holstein, Cincinnati; Carl A. Noble, Maineville, all of Ohio

[73] Assignee: The Procter & Gamble Company, Cincinnati, Ohio

[21] Appl. No.: 496,565

[22] Filed: Jun. 29, 1995

[51] Int. Cl.$^6$ .......................................... A61F 5/00
[52] U.S. Cl. ........................ 602/62; 602/26; 602/63; 607/112
[58] Field of Search ..................... 128/878, 881; 602/2, 26, 62, 5, 13, 20, 21, 23, 60, 61; 2/22, 24, 62, 455; 607/108, 111, 112

[56] References Cited

U.S. PATENT DOCUMENTS

| | | |
|---|---|---|
| 3,149,943 | 9/1964 | Amador . |
| 3,178,724 | 4/1965 | Perschke .................. 473/205 X |
| 3,667,462 | 6/1972 | Moon . |
| 3,736,769 | 6/1973 | Peterson . |
| 3,882,867 | 5/1975 | Moran . |
| 3,893,460 | 7/1975 | Karami . |
| 3,900,035 | 8/1975 | Welch et al. . |
| 3,955,575 | 5/1976 | Okuda . |
| 4,044,773 | 8/1977 | Baldwin, III . |
| 4,081,150 | 3/1978 | Tyson . |
| 4,190,054 | 2/1980 | Brennan . |
| 4,204,543 | 5/1980 | Henderson . |
| 4,243,041 | 1/1981 | Paul . |
| 4,527,566 | 7/1985 | Abare . |
| 4,575,097 | 3/1986 | Brannigan et al. . |
| 4,586,506 | 5/1986 | Nangle . |
| 4,628,918 | 12/1986 | Johnson, Jr. . |
| 4,628,932 | 12/1986 | Tampa . |
| 4,669,476 | 6/1987 | Gordon et al. . |
| 4,671,267 | 6/1987 | Stout . |
| 4,706,658 | 11/1987 | Cronin . |
| 4,802,667 | 2/1989 | Altner .................. 272/123 |
| 4,805,620 | 2/1989 | Meistrell . |
| 4,860,748 | 8/1989 | Chiurco et al. . |
| 4,886,063 | 12/1989 | Crews . |
| 4,914,717 | 4/1990 | Gibbon . |
| 4,961,418 | 10/1990 | McLaurin-Smith . |
| 4,972,832 | 11/1990 | Trapini et al. . |
| 4,981,135 | 1/1991 | Hardy . |
| 5,000,176 | 3/1991 | Daniel . |

(List continued on next page.)

FOREIGN PATENT DOCUMENTS

| | | |
|---|---|---|
| 0 014 300 A1 | 8/1980 | European Pat. Off. . |
| 0 324 578 A1 | 7/1989 | European Pat. Off. . |
| 0 370 600 A1 | 5/1990 | European Pat. Off. . |
| 2 687 912 A1 | 9/1993 | France . |
| 2 205 496 | 12/1988 | United Kingdom . |
| WO 94/00087 | 1/1994 | WIPO . |
| WO 94/12125 | 6/1994 | WIPO . |

*Primary Examiner*—Lynne A. Reichard
*Assistant Examiner*—Kim M. Lee
*Attorney, Agent, or Firm*—Ronald W. Kock

[57] ABSTRACT

A substantially rectangular piece of flexible web having a first end and a second end and an elastic portion therebetween stretchable along a longitudinal axis of the piece of flexible web. The piece of flexible web has a length great enough to encircle a user's knee such that the first and second ends overlap. The first end has a reclosable fastening system for attaching the first end to the piece of flexible web near the second end in order to hold the piece of flexible web around the user's knee when the piece of web is stretched. The piece of flexible web also has an aperture therein. The aperture is aligned with the user's patella to establish a convenient locating point for wrapping the knee wrap around the user's knee. The piece of flexible web further includes a means for extending the piece of flexible web transverse to said longitudinal axis at the aperture in order to accommodate bending of the user's knee. The knee wrap even further includes a plurality of thermal elements embedded in the piece of flexible web. The plurality of thermal elements has a pattern which applies thermal energy to the sides and top of the user's knee.

19 Claims, 2 Drawing Sheets

U.S. PATENT DOCUMENTS

| | | | |
|---|---|---|---|
| 5,007,416 | 4/1991 | Burns et al. | |
| 5,027,801 | 7/1991 | Grim. | |
| 5,062,269 | 11/1991 | Siegel. | |
| 5,065,758 | 11/1991 | Whitehead et al. | |
| 5,072,598 | 12/1991 | Dibrell. | |
| 5,086,629 | 2/1992 | Dibrell. | |
| 5,086,761 | 2/1992 | Ingram | 602/26 |
| 5,088,487 | 2/1992 | Turner. | |
| 5,088,549 | 2/1992 | Schneider. | |
| 5,094,238 | 3/1992 | Gibbon. | |
| 5,133,348 | 7/1992 | Mayn. | |
| 5,165,402 | 11/1992 | McCoy. | |
| 5,179,944 | 1/1993 | McSymytz. | |
| 5,190,033 | 3/1993 | Johnson. | |
| 5,211,623 | 5/1993 | Sarkozi. | |
| 5,269,023 | 12/1993 | Ross. | |
| 5,366,491 | 11/1994 | Ingram et al. | |
| 5,373,582 | 12/1994 | Dragone et al. | |
| 5,375,261 | 12/1994 | Lipke. | |
| 5,378,225 | 1/1995 | Chatman, Jr. | 602/19 |
| 5,398,667 | 3/1995 | Witt. | |
| 5,399,130 | 3/1995 | Saunders | 602/19 |
| 5,451,201 | 9/1995 | Prengler | 602/26 |
| 5,496,357 | 3/1996 | Jensen et al. | 607/108 |
| 5,500,959 | 3/1996 | Yewer, Jr. | 602/19 |
| 5,534,021 | 7/1996 | Dvoretzky et al. | 607/112 |

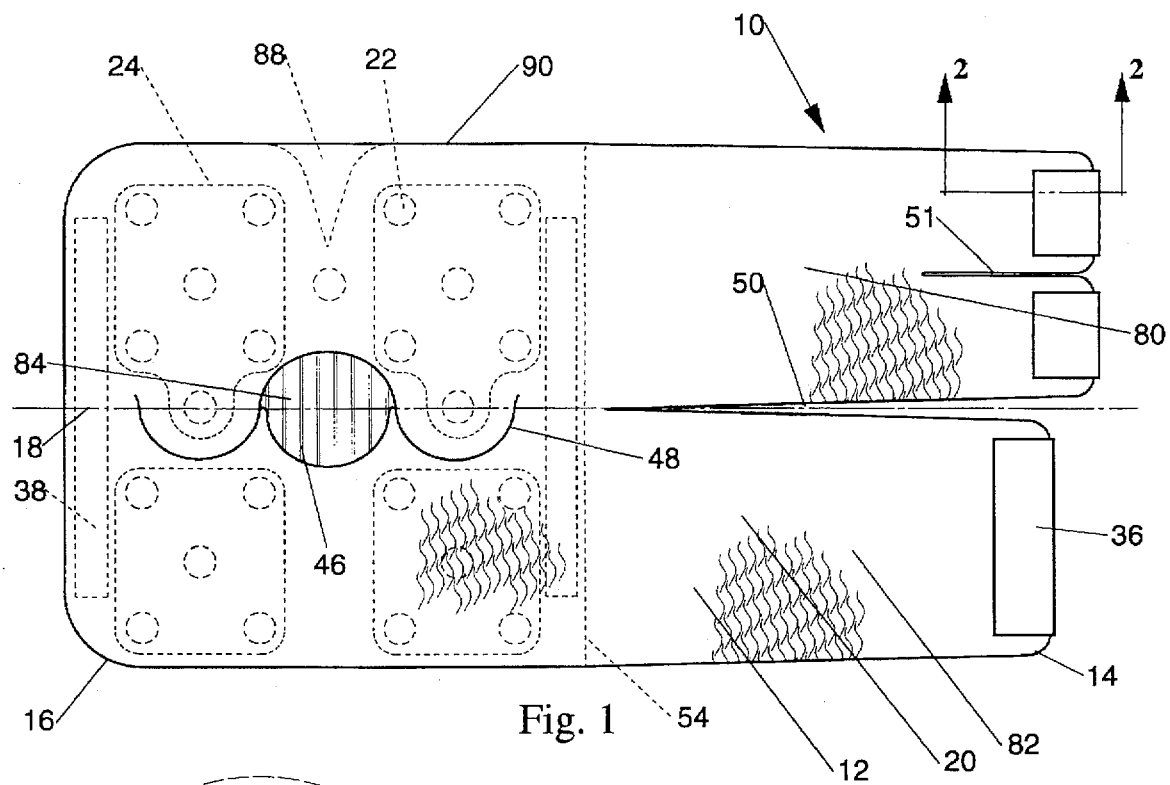
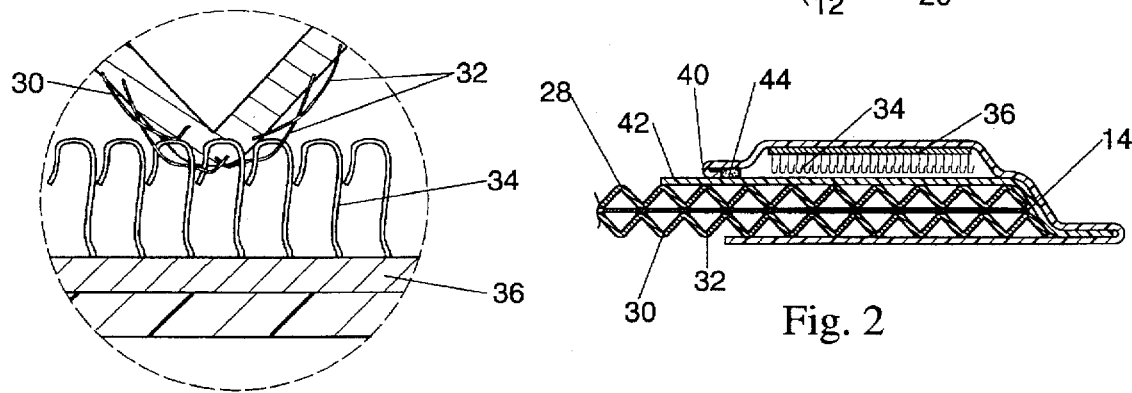
Fig. 3B
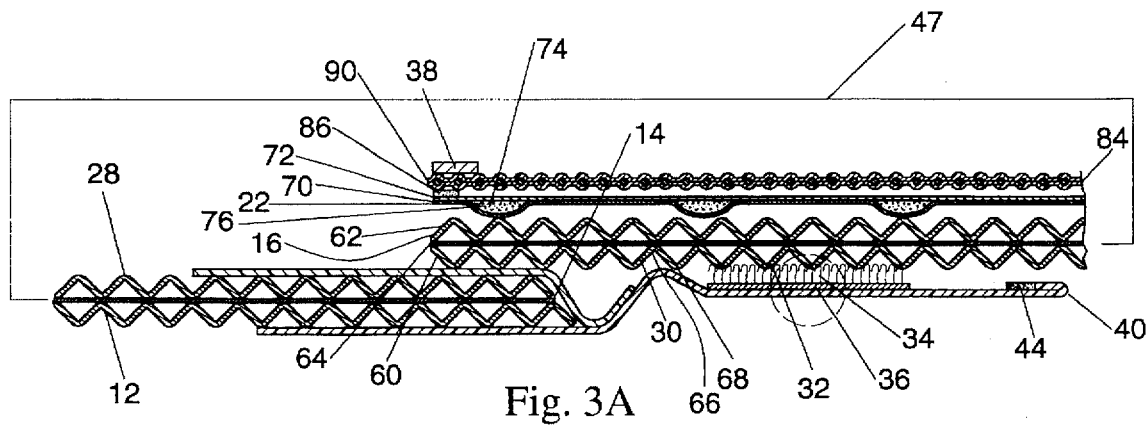
Fig. 3A

ELASTIC KNEE WRAP

FIELD OF THE INVENTION

The present invention relates to knee wraps having thermal sources for pain relief, and more particularly to knee wraps wherein the heating or cooling is applied to specific areas of the user's knee. Even more particularly, the present invention relates to elastic knee wraps having alignment features to position and secure the thermal pattern in the desired location while enabling knee flexure to occur.

BACKGROUND OF THE INVENTION

The human knee is one of the most vulnerable joints of the human body to overstress injury. Heating pads and ice packs are common devices used to relieve the pain of knee injury. Compression provided by elastic bandages also helps to stabilize knee movement during injury healing. However, these pain relieving and stabilization devices typically provide either one function or the other, but not both. Furthermore, heating pads and ice packs are inconvenient to use on a regular and extended basis because: thermal energy may not be immediately available when needed; thermal energy may not be released in a controllable or sustainable manner; and/or proper positioning of thermal energy elements may not be maintainable during knee flexure.

What is needed is an inexpensive disposable knee wrap which provides both compression and thermal energy, which provides thermal energy in a controlled and sustainable manner, which has alignment and position maintenance features, and which has a thermal element pattern that directs thermal energy to where it has the most pain relief benefit.

SUMMARY OF THE INVENTION

In one aspect of the present invention, an elastic knee wrap comprises a substantially rectangular piece of flexible web having a first end and a second end and an elastic portion therebetween stretchable along a longitudinal axis of the piece of flexible web. The piece of flexible web has a length great enough to encircle a user's knee such that the first and second ends overlap. The first end has a reclosable fastening system for attaching the first end to the piece of flexible web near the second end in order to hold the piece of flexible web around the user's knee when the piece of web is stretched. The piece of flexible web also has an aperture therein. The aperture is intended to be aligned with the user's patella to establish a convenient locating point for wrapping said knee wrap around the user's knee.

The piece of flexible web further includes a means for extending the piece of flexible web transverse to said longitudinal axis at the aperture in order to accommodate bending of the user's knee. The means for extending the piece of flexible web transverse to the longitudinal axis at the aperture may be at least one slit extending from said aperture.

The knee wrap further comprises a plurality of thermal elements embedded in the piece of flexible web. The plurality of thermal elements has a pattern which applies thermal energy to the sides and top of the user's knee.

The elastic knee wrap may further comprise a layer of material having a perimeter which is attached to the piece of flexible web and is centered around the aperture. The layer of material has elasticity transverse to said longitudinal axis of the piece of flexible web. In addition, a V-shaped cutout in the layer of material may extend from the perimeter toward the longitudinal axis of the piece of flexible web. The cutout minimizes wrinkling of the knee wrap when the user's leg is straightened, such leg straightening causing the dimension of the user's leg above the knee to be changed compared to the bent leg dimension.

The piece of flexible web may have a continuous outer surface having a plurality of loop fibers. The reclosable fastening system has a plurality of hook members permanently attached to the first end which engage the plurality of loop fibers anywhere along the piece of web in order to adjustably connect the knee wrap to a variety of user's leg sizes and attain a comfortable level of elastic tension. A grip tab extends longitudinally beyond the hook members and a release paper is attached to the first end of the piece of flexible web. The grip tab has pressure sensitive adhesive thereon. The hook members are folded onto the release paper such that the adhesive removably secures the grip tab to the release paper until a user is ready to fasten the first end to the elastic portion.

Also, the first end of the piece of flexible web and the fastening system may include a slit therethrough. The slit extends substantially parallel to the longitudinal axis in order to generate a plurality of independently fastenable first ends. The plurality of independently fastenable first ends provide improved knee wrap adjustability.

The elastic knee wrap may further include a means for increasing friction between the knee wrap and a user's leg in order to reduce slippage of the wrap during use. The knee wrap has a body-facing side and the means is attached to the body-facing side of the knee wrap. The means for increasing friction may include either a strip of foamed polymer attached transverse to the longitudinal axis of the piece of flexible web or a stripe of high-tack polymer printed transverse to the longitudinal axis of the piece of flexible web or both.

In another aspect of the present invention, an elastic knee wrap comprises a substantially rectangular piece of flexible web having a first end and a second end and an elastic portion therebetween stretchable along a longitudinal axis of the piece of flexible web. The piece of flexible web has a length great enough to encircle a user's knee such that the first and second ends overlap. The first end has a reclosable fastening system for attaching the first end to the piece of flexible web near the second end in order to hold the piece of flexible web around the user's knee when the piece of flexible web is stretched. The elastic knee wrap also includes a layer of material the perimeter of which is attached to the piece of flexible web near the second end. The layer of material has elasticity transverse to the longitudinal axis of the piece of flexible web. The piece of flexible web has an aperture therein, within the perimeter of the layer of material, and at least one slit extending from the aperture. The aperture is intended to be aligned with the user's patella, to establish a convenient locating point for wrapping the knee wrap around the user's knee. The aperture and at least one slit enable the layer of material to expand transverse to the longitudinal axis of the piece of flexible material in order to accommodate bending of the user's knee.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 1 is a top plan view of a preferred embodiment of the elastic knee wrap of the present invention, showing the preferred pattern of thermal units embedded therein;

FIG. 2 is a sectioned side elevation view thereof, taken along section line 2—2 of FIG. 1, disclosing a hook fastener connected at one end of the wrap and folded over against a release paper to prevent inadvertent engagement of the hooks with the wrap material, and the lamination structure of the wrap;

FIG. 3A is a sectioned side elevation view thereof, similar to FIG. 2, disclosing the hook fastener end of the wrap overlapping and engaging another portion of the wrap;

FIG. 3B is an enlarged view of a portion of FIG. 3A, disclosing hook and loop fiber engagement at rugosities of the continuous outer surface of the knee wrap.

DETAILED DESCRIPTION OF THE INVENTION

Figure 4:
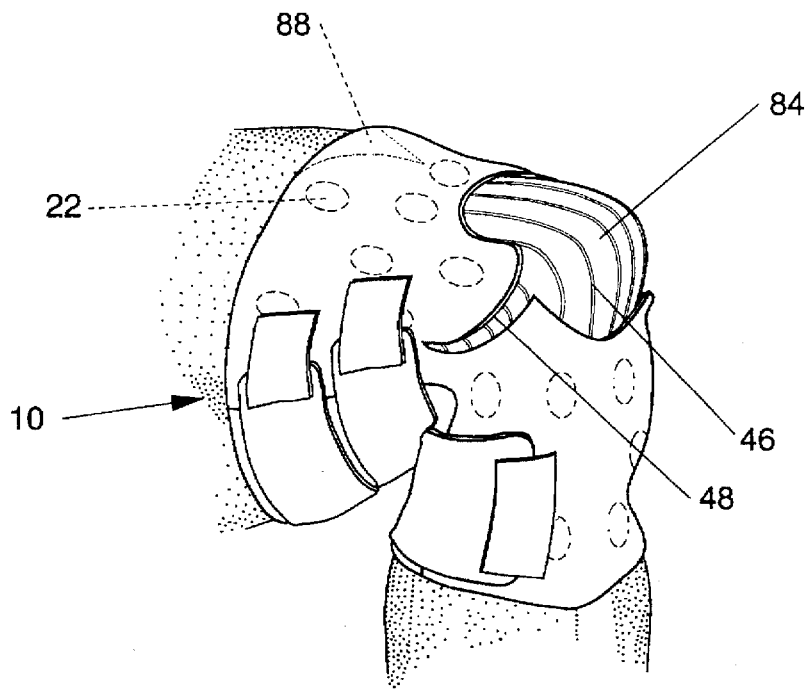
FIG. 4 is a perspective view thereof, showing the knee wrap applied to a user's leg while the leg is bent, with the fastening portion at the front of the user's leg.
Figure 5:
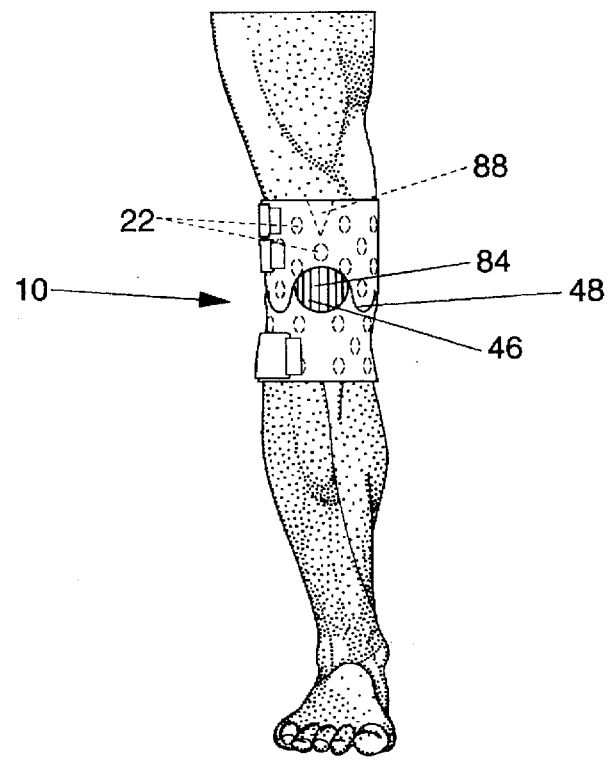
FIG. 5 is a perspective view thereof, showing the location of the knee wrap applied to a user's knee while the leg is straight.

Referring now to the drawings, and more particularly to FIGS. 1 and 2, there is shown a first preferred embodiment of the present invention, which provides an elastic knee wrap, which is generally indicated as 10. As used herein elastic refers to that property of a material whereby the material, when subjected to a tensile force, will stretch or expand in the direction of the force and will essentially return to its original untensioned dimension upon removal of the force. Elastic knee wrap 10 is comprised of a substantially rectangular piece of flexible web 12 having a longitudinal axis 18. Flexible web 12 has a first end 14 and a second end 16 and an elastic portion 20 therebetween capable of being stretched along longitudinal axis 18. Flexible web 12 has a length, as measured in a direction parallel to longitudinal axis 18 from first end 14 to second end 16, which is great enough to encircle a user's knee such that first end 14 overlaps second end 16. Flexible web 12 of knee wrap 10 has a body-facing side 28 and a continuous outer surface 30 extending from first end 14 to second end 16.

Continuous outer surface 30 of wrap 10 contains a plurality of loop fibers 32 disposed along longitudinal axis 18. Plurality of loop fibers 32 serve as the loop member of a reclosable hook and loop fastening system. As used herein the term reclosable refers to that property of a fastening system which provides for initial closing of the fastening system, a subsequent opening of the fastening system, followed by at least one additional closings of the same fastening system. The subsequent closing of the fastening system may either return the closure to the original position or it may result in a repositioning of the closure from the initial configuration. Body-facing side 28 of web 12 contains a plurality of hooks 34 defining hook member 36 which is permanently connected to body-facing side 28 adjacent first end 14. As used herein, the term permanently connected is defined as the joining of two or more elements which remain joined during their intended use. Hook member 36 on body-facing side 28 together with plurality of loop fibers 32 on outer surface 30 provide a reclosable hook and loop fastening system for securing first end 14 of web 12 to outer surface 30 of web 12 to hold wrap 10 in position when flexible web 12 is stretched around the user's knee, such that overlapping first end 14 engages second end 16, as depicted in FIG. 4.

Referring to FIG. 3A, flexible web 12 is shown encircling a user's knee via centerline 47, with first end 14 overlapping second end 16. This overlapping of web 12 positions hook member 36 on side 28 over loop fibers 32 of surface 30. In FIG. 3B, hook member 36 on side 28 is depicted engaging with loop fibers 32 on surface 30. This engagement of hook member 36 with loop fibers 32 forms the hook and loop fastening system which maintains the elastic wrap 10 around the knee of the user. Since loop fibers 32 are disposed continuously along longitudinal axis 18, hook member 36 may be engaged with loop fibers 32 at any position along continuous outer surface 30 of web 12.

Since hook member 36 is capable of engaging loop fibers 32 at any point along web 12 it is desired that hooks 34 be protected from engaging with loops 32 prior to application by the user. In a preferred embodiment of the present invention hook member 36 is affixed to a grip tab 40, said grip tab 40 extending longitudinally beyond hook member 36 adjacent first end 14. Prior to use, grip tab 40, with hook member 36 attached is folded against and removably secured against a release paper 42 by a pressure sensitive adhesive strip 44 extending generally the width of grip tab 40 in a direction transverse to longitudinal axis 18, as depicted in FIG. 2. Release paper 42 remains attached to web 12 at first end 14 throughout application and use. Upon application the user positions wrap 10 and then removes grip tab 40, with hook member 36 attached thereto, from release paper 42. The removal of grip tab 40 from release paper 42 exposes hook member 36 which is then engaged with loop fibers 32 as depicted in FIG. 3B.

Hooks 34 may be any number of styles, shapes, and/or densities depending upon the use. Hooks 34 may be bent shafts as in FIG. 2, mushroom capped, harpoon-shaped, or any other suitable shape. Hooks 34 may be unidirectional, bi-directional, or omni-directional depending upon the application and companion loop fibers 32. Hooks 34 must be chosen in conjunction with companion loop fibers 32 so as to provide the peel and shear forces that are required for different applications.

Flexible web 12 further has an interfacial centerline 54 aligned perpendicular to longitudinal axis 18 located between first end 14 and second end 16. Flexible web 12 further has an aperture 46 between interfacial centerline 54 and second end 16. Aperture 46 is intended to be aligned with the wearer's patella and serves to help properly position wrap 10 during application. Extending from aperture 46, web 12 has at least one slit 48. Preferably two slits 48 extend from aperture 46, one toward second end 16 and the other toward interfacial centerline 54. Slits 48 allow web 12 to expand and close respectively as the user bends and straightens the knee.

Preferably, elastic knee wrap 10 further comprises a layer of material 84 located preferably on body-facing side 28 of web 12. Layer of material 84 is generally coextensive web 12 from second end 16 to interfacial centerline 54. Material 84 has elasticity in a direction transverse to longitudinal axis 18 of web 12. Preferably, material 84 has an elastic recovery force which is as low as possible to minimize forces transverse to longitudinal axis 18 So that web 12 will not be bunched or pulled off the upper leg when the user's knee is flexed. Layer of material 84 is attached to body-facing side 28 of web 12 along the perimeter 90 of material 84 using adhesive 86 as depicted in FIG. 3B. Material 84 provides coverage of the knee when the user's knee is bent and web 12 expands separating slits 48, as depicted in FIG. 4.

Material layer 84 may be any number of suitable materials. One material that has been used successfully is a trilaminate made from two layers of carded, thermally bonded polypropylene (TBPP) nonwoven and an elastic scrim therebetween. The nonwoven used is a 27 gsy nonwoven available from Fibertech of Landisville, N.J. as white TBPP, brand #67050. The scrim used is from Conwed Plastics of Minneapolis, Minn. as TN4631 plastic netting. All three layers are assembled using a pressure sensitive hot melt glue available from Findley Adhesives, Wawautosa, Wis. as 2031 adhesive. The glue is applied via a spiral application method by Waytek of Springboro, Ohio at a level of 0.002 to 0.006 grams per square inch. The trilaminate is assembled with the elastic scrim under zero strain. The assembled trilaminate is then passed between a pair of matched ring rolls with an egagement of about 2 mm to break the nonwoven on a fine scale and allow the elastic scrim to stretch.

Material 84 is attached along perimeter 90 to web 12 by a double sided adhesive tape available from 3M of St. Paul, Minn., as 1524 adhesive tape. A variety of different methods could be used to attach material 84 to web 12 including but not limited to: hot melt adhesive, pressure sensitive adhesives, ultrasonic bonding, pressure bonding, etc. Adhesives, if used, can be applied via hot melt beads, foam, spiral hot melt, melt blown, spray, immersion, transfer, etc.

In a particularly preferred embodiment of the present invention, layer of material 84 has a V-shaped cutout extending from perimeter 90 toward longitudinal axis 18 of web 12. V-shaped cutout 88 allows web 12 to stretch in a direction parallel to longitudinal axis 18 in the area of cutout 88 when the user bends the knee. The dimension around the wearer's knee is smaller when the user straightens leg. Cutout 88 provides web 12 with the ability to stretch and recover during the flexing of the knee which minimizes gapping or wrinkling of wrap 10 during wear.

Alternatively material 84 may have elasticity in a direction parallel to longitudinal axis 18 in addition to elasticity in a direction transverse to longitudinal axis 18. The addition of elasticity in a direction parallel to longitudinal axis 18 in material 84 could deliver the desired stretch to web 12 in the area of V-shaped cutout 88 without the need for cutout 88.

Web 12 and hook member 36 and grip tab 40 preferably have a slit 50 therethrough substantially parallel to longitudinal axis 18 starting at first end 14 and extending into web 12. Slit 50 provides web 12 with an upper strap potion 80 and a lower strap portion 82, each containing hook member 36 which can be independently fastened to loop fibers 32. Upper strap portion 80 encircles the user's leg above the knee and lower strap portion 82 encircles the user's leg below the knee when wrap 10 is worn. Upper strap portion 80 and lower strap portion 82 allow easier application and differential tensioning of web 12 during use. Alternatively, upper strap portion 80 and/or lower strap portion 82 may have one or more secondary slits 51 as depicted in FIG. 1. Secondary slit 51 provides differential tensioning of web 12 above and/or below the user's knee. Slit 48 is preferably a sinusoidal shape as depicted in FIG. 1. This particular shape allows for the location of thermal elements 22 on either side of the knee immediately adjacent the user's patella.

Elastic knee wrap 10 also has a plurality of thermal elements 22 arranged in a pattern, as indicated by dotted line 24, which apply thermal energy to the sides and top of the knee when web 12 is stretched around the user's knee. Thermal elements 22 are constructed by thermoforming a base material 70 to form a pocket 76. Pocket 76 in base material 70 is then filled with chemistry 74. After filling pocket 76 in base material 70 with chemistry 74, a cover material 72 is placed over pocket 76 and heat sealed to base material 70 around the periphery of pocket 76, encapsulating chemistry 74. Small holes are then pierced in base material 70 and/or cover material 72 to allow oxygen to reach chemistry 74.

Base material 70 and cover material 72 may be made of any number of materials capable of containing chemistry 74 and limiting oxygen flow into pocket 76. A material that has been used successfully is 42 gram per square meter polypropylene spunbond nonwoven which is extrusion coated with low density polyethylene and/or ethyl vinyl acetate (EVA) at a thickness of 50 to 75 microns. Thermal elements 22 are preferably about 25 mm in diameter and about 6 mm in height. Thermal elements 22 may either be formed individually or in units of two or more. The embodiment shown in FIG. 1 depicts a total of twenty three thermal units 22 delivered in two groups of five each, two groups of six each and an individual cell all shown by pattern line 24.

Chemistry 74 is preferably a mixture of powdered iron, powdered activated charcoal, vermiculite, water, and salt. Mixtures of this type react when exposed to oxygen providing heat for several hours. Prior to use, wrap 10 with thermal elements 22 is enclosed within an oxygen impermeable package. To use, wrap 10 is removed from the oxygen impermeable package allowing oxygen to enter pockets 76 and react with chemistry 74 of thermal elements 22.

Body-facing side 28 of flexible web 12 preferably contains foamed polymer anti-slip strips 38 aligned transverse to longitudinal, axis 18 of web 12 for increasing friction between knee wrap 10 and the wearer's knee. Foamed polymer anti-slip strips 38 are located adjacent second end 16 and interfacial line 54. These two strips are positioned in a relatively low-motion zone of the knee during bending and straightening thereof. They experience relatively little expansion or contraction in a direction transverse to longitudinal axis 18. The increased friction provided by foamed polymer strips 38 serves to reduce slippage or relative movement between knee wrap 10 and the wearer. In a particularly preferred embodiment of the present invention, foamed polymer strips 38 may also be made visually different (e.g. color) from web 12. This difference can be used by the user as a visual aid in identifying body-facing side 28. Anti-slip foamed strips 38 are preferably about 25 mm wide and about 1.5 mm thick. Alternatively, a high-tack polymer such as Ethyl Vinyl Acetate (EVA) may be used instead of foamed polymer strips to provide the high friction and/or visual alignment features. These materials may be glued, thermally bonded or printed onto body-facing side 28.

Flexible web 12 preferably has a first fibrous layer 60 at outer surface 30, a second fibrous layer 62 at body-facing side 28, and an elastic member 64 interposed therebetween. Fibrous layer 60 and fibrous layer 62 may be a number of different materials which include but are not limited to: woven or knit fabrics that have been brushed to increase the "nap" and expose more "loops", through-air bonded nonwovens, carded nonwovens, spunbonded nonwovens, etc.

Elastic member 64 can be selected from natural or synthetic rubber, or any number of polymeric materials which are capable of elongation and recovery. Suitable materials include but are not limited to: Styrene Block Copolymers; rubber; Lycra™, a trademark of E. I. DuPont De Nemours of Wilmington, Del.; Krayton™, a trademark of Shell Oil Co. of Houston, Tex.; polyethylenes including metallocene catalyst PE; foams including polyurethane and polyester;

etc. Elastic member 64 can be in the form of: films, strands, scrims, ribbons, tapes, structural elastic-like film, etc.

Elastic member 64 can be bonded to fibrous layer 60 and 62 in any number of ways including but not limited to: double sided adhesive tapes, hot melt adhesive, pressure sensitive adhesives, ultrasonic bonding, pressure bonding, etc. Adhesives, if used, can be applied via hot melt beads, foam, spiral hot melt, melt blown, spray, immersion, transfer, etc. Suitable elastic properties can be achieved via a number of construction techniques: lamination with strained elastic, zero-strain elastics with subsequent activation in either machine direction or cross direction, or a combination of these techniques.

A preferred method of construction of flexible web 12 is accomplished by first straining elastic member 64 in the longitudinal direction at least thirty percent. That is, the dimension in the longitudinal direction of web 12 when it is strained is at least thirty per cent longer than the unstrained dimension of web 12. While elastic member 64 is held in this strained configuration, fibrous layer 60 and fibrous layer 62 are juxtaposed on either side of elastic member 64 and discontinuously bonded one to another at bond sites 66. Once bonded, elastic member 64 is allowed to relax and return to its unstrained configuration. This relaxing of elastic member 64 causes fibrous layers. 60 and 62 to pucker and form rugosities 68 between bond sites 66. Rugosities 68 of fibrous layer 60 provide a plurality of loop fibers 32 on outer surface 30. Ideally, elastic member 64 is strained sufficiently during assembly of web 12 such-that during normal use the wearer does not fully extend web 12. If web 12 were fully extended during use to the dimension at which it is constructed, the amplitude of rugosities 68 would be minimized, lowering the engagement force between hooks 34 and bop fibers 32.

In a particularly preferred embodiment of the present invention wrap 10 is made using the following materials and method. A film of Styrene Block Copolymer (SBC) is bonded to two layers of polypropylene (PP) spunbond nonwoven. A trilaminate is made by stretching the elastic SBC about 100% (twice its original length). While the SBC is held in this strained position, a layer of PP nonwoven is positioned on either side. The trilaminate is ultrasonically bonded together in a discrete pattern of bond sites spaced about 5 to 7 mm apart. The trilaminate is then released and allowed to return to a relaxed position. The PP nonwoven is gathered or puckered between the bonding sites. An SBC that has been successfully used is a 0.0024 inch (2.4 mil) thick EXX500D which is produced by Exxon Chemicals of Lake Zurich, Ill. Nonwovens that have been successfully used are a 14 gram/square yard (gsy) and a 17 gsy spunbond PP available from Veratec of Walpole, Mass. The combining operation (stretching, combining, bonding) has been done by Veratec of Walpole, Mass. The resulting trilaminate elastic material is available from Veratec as PO671.0. The resulting knee wrap 10 is about 230 mm wide (measured in a direction transverse to longitudinal axis 18) by about 500 mm long.

Hook member 36 and loop fibers 32 ideally are chosen to provide shear strength greater than the elastic tension exerted by wrap 10 during use. Hook member 36 that has been found to work particularly web with the above described elastic loop material comprises harpoon-shaped hooks 34 which are oriented along the longitudinal axis of web 12. Such hooks are available from Aplix of Charlotte, N.C. and are available as 960B. Hooks 34 are made of polypropylene, mounted on a polypropylene base, and are about 0.8 mm in height. These hooks are permanently mounted to grip tab 40, which is folded over onto a release paper. Grip tab 40 is then attached to first end 14 of the wrap. A small strip of adhesive keeps the grip tab closed protecting the hooks until the wearer peels back the grip tab, exposing the hooks during application. The grip tab, with the pressure sensitive adhesive already attached is made by the 3M Company, St. Paul, Minn. and is available as Soft White Fastening Tape, $2^{11}/_{16}$ inch wide. It is available on robs and is then cut in length to fit the width of the wrap to which it is to be applied. The hooks may be attached to the grip tabs with adhesive, ultrasonic bonding, pressure bonding, stitching, or any other suitable means.

Further details concerning the elastic knee wrap of the present invention may be found in copending application entitled "ELASTIC WRAP HAVING NON-TARGETED RECLOSABLE FASTENER", filed on the same day as the present application via U.S. Express Mail EF28076264045, and obligated to be assigned to the assignee of the present application, and which is hereby incorporated by reference.

Thermal elements 22 are preferably heating elements, which are described in a copending application entitled "A HEAT CELL", filed on the same day as the present application via U.S. Express Mail EG08845952245, and obligated to be assigned to the assignee of the present application, and which is hereby incorporated by reference.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. An elastic knee wrap comprising:

a) a piece of flexible web having a first end and a second end and an elastic portion therebetween stretchable along a longitudinal axis of said piece of flexible web, said piece of flexible web having a length great enough to encircle a user's knee during use such that said first and second ends overlap, said first end having a reclosable fastening system for attaching said first end to said piece of flexible web near said second end in order to hold said piece of flexible web around the user's knee when said piece of web is stretched, said piece of flexible web also having an aperture therein, said aperture intended to be aligned with the user's patella to establish a convenient locating point for wrapping said knee wrap around the user's knee, said piece of flexible web further having a slit extending substantially longitudinally from said aperture enabling the user to extend said piece of flexible web transverse to said longitudinal axis at said aperture in order to accomodate bending of the user's knee; and b) a plurality of thermal elements embedded in said piece of flexible web, said plurality of thermal elements having a pattern which applies thermal energy to the user's knee.

2. The elastic knee wrap of claim 1 further comprising a layer of material having a perimeter, said perimeter attached to said piece of flexible web centered around said aperture, said layer of material having elasticity transverse to said longitudinal axis of said piece of flexible web.

3. The elastic knee wrap of claim 2 wherein said layer of material has a V-shaped cutout extending from said perimeter toward said longitudinal axis of said piece of flexible web, said cutout minimizing wrinkling of said knee wrap when the user's leg is straightened, such leg straightening causing the dimension of the user's leg above the knee to be changed compared to the bent leg dimension.

4. The elastic knee wrap of claim 1 wherein said piece of flexible web has a continuous outer surface having a plurality of loop fibers and said reclosable fastening system has a plurality of hook members permanently attached to said first end which engage said plurality of loop fibers anywhere along said piece of web in order to adjustably connect said knee wrap to a variety of user's leg sizes and attain a comfortable level of elastic tension.

5. The elastic knee wrap of claim 4 further comprising a grip tab extending longitudinally beyond said hook members and a release paper attached to said first end of said piece of flexible web, said grip tab having pressure sensitive adhesive thereon, said hook members being folded onto said release paper such that said adhesive removably secures said grip tab to said release paper until a user is ready to fasten said first end to said elastic portion.

6. The elastic knee wrap of claim 1 further comprising a means for increasing friction between said knee wrap and a user's leg in order to reduce slippage of said wrap during use, wherein said knee wrap has a body-facing side and said means is attached to said body-facing side of said knee wrap.

7. The elastic knee wrap of claim 6 wherein said means for increasing friction comprises a strip of foamed polymer attached transverse to said longitudinal axis of said piece of flexible web, said strip also providing resistance to knee wrap bunching during knee flexing.

8. The elastic back wrap of claim 6 wherein said means for increasing friction comprises a stripe of high-tack polymer printed, transverse to said longitudinal axis of said piece of flexible web.

9. The elastic knee wrap of claim 1 wherein said first end of said piece of web and said fastening system have a slit therethrough, said slit extending substantially parallel to said longitudinal axis in order to generate a plurality of independently fastenable first ends, said plurality of independently fastenable first ends providing improved knee wrap adjustability.

10. An elastic knee wrap comprising:
a) a piece of flexible web having a first end and a second end and an elastic portion therebetween stretchable along a longitudinal axis of said piece of flexible web, said piece of flexible web having a length great enough to encircle a user's knee during use such that said first and second ends overlap, said first end having a reclosable fastening system for attaching said first end to said piece of flexible web near said second end in order to hold said piece of flexible web around said user's knee when said piece of flexible web is stretched; and
b) a layer of material having a perimeter, said perimeter attached to said piece of flexible web near said second end, said layer of material having elasticity transverse to said longitudinal axis of said piece of flexible web, said piece of flexible web within said perimeter of said layer of material having an aperture therein and at least one slit extending substantially longitudinally from said aperture, said aperture intended to be aligned with the user's patella, to establish a convenient locating point for wrapping said knee wrap around the user's knee, said at least one slit and aperture enabling said layer of material to expand transverse to said longitudinal axis of said piece of flexible material in order to accomodate bending of the user's knee.

11. The elastic knee wrap of claim 10 further comprising a plurality of thermal elements embedded in said piece of flexible web, said plurality of thermal elements having a pattern which applies thermal energy to the sides and top of the user's knee.

12. The elastic knee wrap of claim 10 wherein said piece of flexible web has a continuous outer surface having a plurality of loop fibers and said reclosable fastening system has a plurality of hook members permanently attached to said first end which engage said plurality of loop fibers anywhere along said piece of flexible web in order to adjustably connect said knee wrap to a variety of user's leg sizes and attain a comfortable level of elastic tension.

13. The elastic knee wrap of claim 12 further comprising a grip tab extending longitudinally beyond said hook members and a release paper attached to said first end of said piece of flexible web, said grip tab having pressure sensitive adhesive thereon, said hook members being folded onto said release paper such that said adhesive removably secures said grip tab to said release paper until a user is ready to fasten said first end to said elastic portion.

14. An elastic knee wrap comprising:
a) a piece of flexible web having a first end and a second end and an elastic portion therebetween stretchable along a longitudinal axis or said piece of flexible web, said piece of flexible web having a length great enough to encircle a user's knee during use such that said first and second ends overlap, said first end having a reclosable fastening system for attaching said first end to said piece of flexible web near said second end in order to hold said piece of flexible web around said user's knee when said piece of flexible web is stretched, said piece of flexible web also having an aperture therein, said aperture intended to be aligned with the user's patella to establish a convenient locating point for wrapping said knee wrap around the user's knee, said piece of flexible web further having a slit extending substantially longitudinally from said aperture enabling the user to extend said piece of flexible web transverse to said longitudinal axis at said aperture in order to accomodate bending of the user's knee, said piece of flexible web also having a continuous outer surface having a plurality of loop fibers and said reclosable fastening system having a plurality of hook members permanently attached to said first end which engage said plurality of loop fibers anywhere along said piece or flexible web in order to adjustably connect said knee wrap to a variety of user's leg sizes and attain a comfortable level of elastic tension;
b) a plurality of thermal elements embedded in said piece of flexible web, said plurality of thermal elements having a pattern which applies thermal energy to the user's knee; and
c) a means for increasing friction between said knee wrap and a user's leg in order to reduce slippage of said wrap during use, wherein said knee wrap has a body-facing side and said means is attached to said body-facing side of said knee wrap.

15. The elastic knee wrap of claim 14 further comprising a layer of material having a perimeter, said perimeter attached to said piece of flexible web centered around said aperture, said layer of material having elasticity transverse to said longitudinal axis of said piece of flexible web.

16. The elastic knee wrap of claim 15 wherein said layer of material has a V-shaped cutout extending from said perimeter toward said longitudinal axis of said piece of flexible web, said cutout minimizing wrinkling of said knee wrap when the user's leg is straightened, such leg straightening causing the dimension of the user's leg above the knee to be changed compared to the bent leg dimension.

17. The elastic knee wrap of claim 14 further comprising a grip tab extending longitudinally beyond said hook members and a release paper attached to said first end or said piece of flexible web, said grip tab having pressure sensitive adhesive thereon, said hook members being folded onto said release paper such that said adhesive removably secures said grip tab to said release paper until a user is ready to fasten said first end to said elastic portion.

18. The elastic knee wrap of claim 14 wherein said first end of said piece of web and said fastening system have a slit therethrough, said slit extending substantially parallel to said longitudinal axis in order to generate a plurality of independently fastenable first ends, said plurality of independently fastenable first ends providing improved knee wrap adjustability.

19. The elastic knee wrap of claim 14 wherein said means for increasing friction comprises a strip of foamed polymer attached transverse to said longitudinal axis of said piece of flexible web, said strip also providing resistance to knee wrap bunching during knee flexing.

* * * * *

UNITED STATES PATENT AND TRADEMARK OFFICE
CERTIFICATE OF CORRECTION

PATENT NO. : 5,728,058

DATED : March 17, 1998

INVENTOR(S) : Ouellete et al.

It is certified that error appears in the above-identified patent and that said Letters Patent is hereby corrected as shown below:

Claim 8, line 31, "printed" should read --aligned--.

Claim 10, line 49, "said user's" should read --the user's--.

Claim 14, line 23, "or" should read --of--.

Claim 14, line 28, "said user's" should read --the user's--.

Claim 17, line 3, "or" should read --of--.

Signed and Sealed this

Twenty-eighth Day of July, 1998

Attest:

BRUCE LEHMAN

Attesting Officer

Commissioner of Patents and Trademarks